(12) United States Patent
McGrew

(10) Patent No.: US 6,974,681 B1
(45) Date of Patent: Dec. 13, 2005

(54) CELL CULTURE PERFORMANCE WITH VANADATE

(75) Inventor: Jeffrey T McGrew, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 351 days.

(21) Appl. No.: 10/226,669

(22) Filed: Aug. 23, 2002

(51) Int. Cl.$^7$ .................. C12N 15/06; C12N 15/09
(52) U.S. Cl. .................. 435/41; 435/325; 435/69.1; 435/440; 514/2; 514/7
(58) Field of Search .................. 435/41, 69.1, 69.2, 435/440, 325; 530/350, 402; 514/7, 2

(56) References Cited

U.S. PATENT DOCUMENTS

| | | | |
|---|---|---|---|
| 4,680,261 A * | 7/1987 | Nobuhara et al. ......... 435/70.5 |
| 5,705,364 A | 1/1998 | Etcheverry et al. | |
| 5,958,957 A * | 9/1999 | Andersen et al. ........... 514/364 |
| 6,020,374 A * | 2/2000 | Geier et al. ................. 514/553 |
| 6,784,205 B2 * | 8/2004 | Wiesmann et al. ......... 514/469 |

OTHER PUBLICATIONS

Kazazi, F. et al. (19960 Activation of the HIV long terminal repeat and viral production by H2O2-vanadate.☐☐Free Radic Biol Med. vol. 20, pp. 813-820.*

Yoshida, A. et al. (2002) Orthovanadate decreases the leptin content in isolated mouse fat pads via proteasome activation. ☐☐Arch Biochem. Biophys. vol. 406, pp. 253-260.*

Zhande, R. et al. (2002) Molecular mechanism of insulin-induced degradation of insulin receptor substrate 1.☐☐Mol Cell Biol. vol. 22, pp. 1016-1026.*

Posner, et al., Peroxovanadium Compoumds J. of Biol Chem 269:4596-5604 (1994).

Sekar et al., Vanadium Salts as Insulin Substitutes: Mechansim of Action, a Scientific and Therapeutic Tool in Diabetes Mellitus Research Crit Rev Biochem Mol Biol 31(5)339-359 (1996).

Barbeau et al., Activation of HIV-a Long Terminal Repeat Transcription and Virus Replication via NF-kB-dependent and -independent Pathways by Patent Phosphotyrosine Phosphatase Inhibitors, the Peroxovanadium Compounds J. of Biol Chem 272-12968-12977 (1997).

Huyer et al., Mechanism of Inhibition of Protein-tyrosine Phosphatases by Vanadate and Pervanadate J. of Biol Chem 272:843-851 (1997).

Rasmussen et al.,Isolation, characterization and recombinant protein expression in Veggie-CHO: A serum-free CHO host cell line Cytotechnology 28:31-42 (1998).

Lee-Kwon et al., Antiapoptotic Signaling by the Insulin Receptor in Chinese Hamster Ovary Cells Biochemistry 37:15747-15757 (1998).

Pandey et al., Phosphatidylinositol 3-Kinase Requirement in Activation of the ras/C-raf-1/MEK/ERK and p70$^{th}$ Signaling Cascade by the Insulinomimetic Agent Vanadyl Sulfate Biochemistry 38:14667-14675 (1996).

* cited by examiner

*Primary Examiner*—Jon Weber
*Assistant Examiner*—Samuel W. Liu
(74) *Attorney, Agent, or Firm*—Marshall, Gerstein & Borun LLP

(57) ABSTRACT

The invention provides methods and compositions for improved in vitro culture of cells that make use of vanadate. The methods enhance cell survival thereby recovery of the polypeptide of interest produced in the cells is increased relative to cells grown without vanadate.

38 Claims, 1 Drawing Sheet

CELL CULTURE PERFORMANCE WITH VANADATE

FIELD OF THE INVENTION

This invention relates generally to the field of cell culture. More particularly, the invention relates to improving yields of secreted polypeptides by the addition of vanadate ions to tissue culture media. In addition, the methods and compositions of the invention allow for reduction of the use of growth factors in culture media.

BACKGROUND

Many commercially important polypeptides are recombinantly produced in cells grown in culture. One of the limits to growing cells in culture is the decreased viability of the cells over time, which is partially rectified by the addition of an extracellular signal, such as a growth factor. However, while this extra step improves cell viability, it adds significant costs to the production of the desired recombinant polypeptide.

Cellular responses to extracellular signals such as growth factors are controlled, in part, by post-translational modifications of polypeptides expressed on the cell surface and/or in the cell cytoplasm. Highly dependable regulation of post-translational modifications is important in maintaining the integrity of normal cell signaling. Kinases, which add phosphates to substrates, and phosphatases, which remove phosphates from phosphorylated substrates, are two large classes of enzymes regulating post-translational modifications of cellular machinery that are frequently mutated in human disease (Schlessinger (2000) Cell, 103(2):211–25; Fischer et al., (1991) Science, 253:401–6; Hunter (1998–99) Harvey Lect., 94:81–119).

The study of phosphorylation regulation has led to the identification of numerous non-proteinaceous compounds that inhibit or activate enzymes. One such compound, vanadate, has been identified as a molecule which has a specific inhibitory activity toward tyrosine phosphatases. Vanadate ions have been shown to also act as insulin mimics in animal cells by an as yet unknown mechanism (Pandey et al., (1999) Biochemistry, 38:14667–14675; Posner et al., (1994) J. Biol. Chem., 269:4596–4604; Huyer et al., (1997) J. Biol. Chem., 272:843–851; Scheving et al., (1999) Am. J. Physiol., 277: C572–9). Vanadate has also been shown to inhibit apoptosis in a mammalian cell line subjected to serum withdrawal in an insulin receptor independent manner (Lee-Kwon et al., (1998) Biochemistry, 37:15747–15757). However, vanadate has been shown to have toxicity in humans and other mammals when tested for use as an insulin substitute (see generally, Sekar et al., (1996) Crit. Rev. Biochem. Mol. Biol., 31(5):339–359). Nobuhara et al. (U.S. Pat. No. 4,680, 261) added vanadate, among other metals, to non-recombinant cell cultures producing endogenous interferons.

Thus, there is a need in the art for methods of improving the cell viability of recombinant cell cultures to reduce cell death, to reduce the dependence on growth factors and to increase recombinant polypeptide production while minimizing costs. The invention fulfills this need by providing a simple, easy and inexpensive way of increasing recombinant cell viability and reducing the requirement for growth factors by cultured animal cells.

SUMMARY OF THE INVENTION

In the invention provided herein, vanadate is added to medium used for culturing recombinant polypeptide producing animal cells in vitro. Cell cultures grown in such medium demonstrated significantly increased cell numbers, cell viability, and recombinant polypeptide production. Consequently, the quantity of required growth factors added in cultured cell growth was reduced for vanadate treated cell cultures, and culture performance was improved.

Accordingly, in one aspect, the invention provides a method comprising culturing cells in tissue culture medium containing an effective amount of vanadate. While any cell type can benefit, mammalian cells find particular benefit from growth according to the invention, and particularly CHO cells. The vanadate can be, for example, orthovanadate, pervanadate or peroxovanadate or any derivative thereof. The invention finds particular use in the culturing of cells that are genetically engineered to secrete a polypeptide of interest.

In another aspect, the invention provides for recombinant vectors having nucleic acids expressing polypeptides of interest, wherein the nucleic acids are operably linked to a promoter and/or enhancer responsive to vanadate.

In a related aspect, the invention also provides a cell culture comprising cells recombinantly engineered to secrete a polypeptide of interest in vitro, and an effective amount of vanadate sufficient to increase cell viability and to increase recovery of the polypeptide of interest.

DETAILED DESCRIPTION OF THE INVENTION

Figure 1:
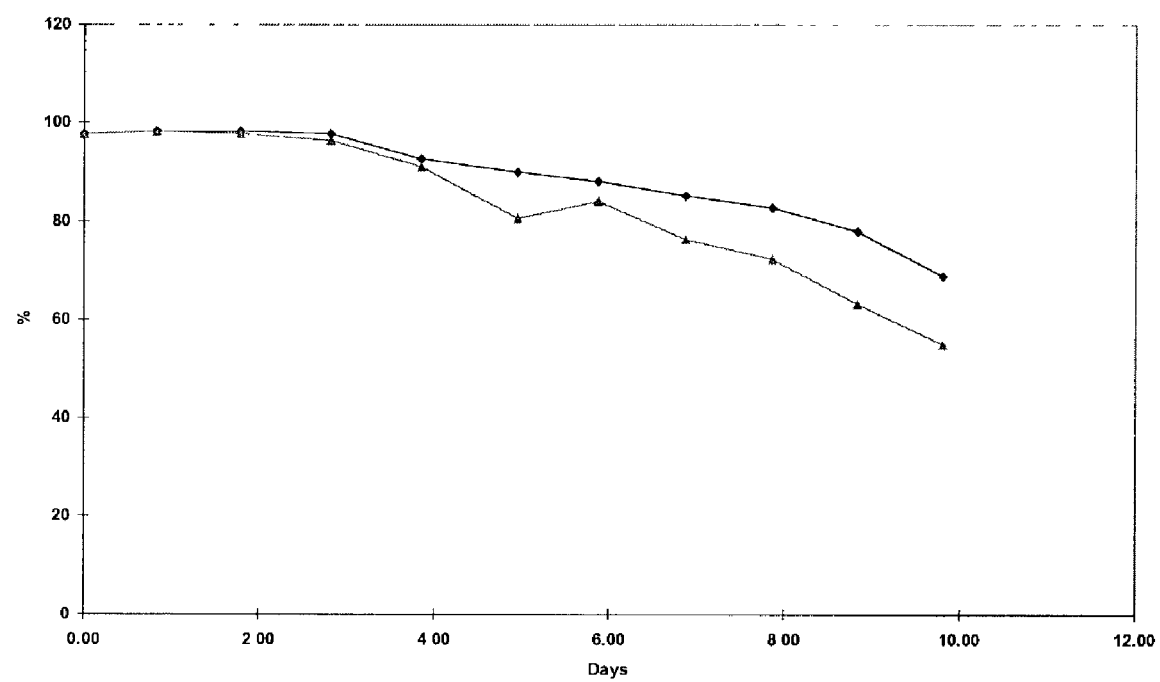
FIG. 1. Addition of sodium orthovanadate to a recombinant cell culture (expressing huTNFR-Fc) reduces the requirement for IGF-1 to maintain viability in a balanced feed experiment. Diamonds show viability of culture with 25 $\mu$g/L IGF-1 with 20 $\mu$M sodium orthovanadate, and the triangles show results of 100 $\mu$g/L IGF-1 without vanadate.

The invention is based, in part, on the discovery that vanadate can be used in vitro to improve the performance and growth of animal cell cultures. Specifically, vanadate acts to reduce cell death and to increase recombinant polypeptide production of cell cultures, thereby enhancing culture robustness, and also reduces the reliance on the addition of growth factors to the medium, thereby reducing costs associated with recombinant polypeptide production.

In illustrative, non-limiting examples described below, orthovanadate was used as a model compound to increase cell viability and increase polypeptide production in a recombinant mammalian cell culture system. In particular, it is shown that addition of vanadate to the medium increases cell viability and production of recombinant polypeptides. These results demonstrate that vanadate can be used to substantially improve the performance of in vitro animal cell culture systems.

While the working examples provide a description of animal cells grown in the presence of vanadate that demonstrate improved viability concomitant with improved production of recombinant polypeptides, it will be understood by one of skill in the art that non-animal cells such as prokaryotic cells, e.g., *E. coli*, insect cells, e.g., S*f*9, plant cells, yeast cells or the like can also be grown in the presence of vanadate such that viability is improved and recombinant production of polypeptides is enhanced. However, the invention is particularly advantageous for growing industrially important animal cell lines that have been adapted to grow in long-term culture and are producing recombinant polypeptides of interest.

By animal cell is meant a cell whose progenitors were derived from a multicellular animal. Preferably, the animal cell lines are mammalian cell lines. A wide variety of animal cell lines suitable for growth in culture are available from, for example, the American Type Culture Collection (ATCC, Manassas, Va.) and NRRL (Peoria, Ill.). Some of the more established cell lines typically used in the industrial or academic laboratory and which are preferred are CHO, VERO, BHK, HeLa, Cos, CV1, MDCK, 293, 3T3, PC 12, hybridoma, myeloma, and W138 cell lines, to name but a few examples. The dihydrofolate reductase (DHFR)-deficient mutant cell line (Urlaub et al., 1980, Proc Natl Acad Sci USA 77:4216–4220), DXB11 and DG-44, are the CHO host cell lines of choice because the efficient DHFR selectable and amplifiable gene expression system allows high level recombinant polypeptide expression in these cells (Kaufman R. J., 1990, Meth Enzymol 185:527–566). In addition, these cells are easy to manipulate as adherent or suspension cultures and exhibit relatively good genetic stability. In addition, new animal cell lines can be established using methods well known by those skilled in the art (e.g., by transformation, viral infection, and/or selection, etc.).

By in vitro cell culture is meant the growth and propagation of cells outside of a multicellular organism or tissue. Typically, in vitro cell culture is performed under sterile, controlled temperature and atmospheric conditions in tissue culture plates (e.g., 10 cm plates, 96 well plates, etc.), or other adherent culture (e.g., on microcarrier beads) or in suspension culture such as in roller bottles. Cultures can be grown in shake flasks, small scale bioreactors, and/or large-scale bioreactors. A bioreactor is a device used to culture animal cells in which environmental conditions such as temperature, atmosphere, agitation, and/or pH can be monitored and adjusted. A number of companies (e.g., ABS Inc., Wilmington, Del.; Cell Trends, Inc., Middletown, Md.) as well as university and/or government-sponsored organizations (e.g., The Cell Culture Center, Minneapolis, Minn.) offer cell culture services on a contract basis.

Further, the recombinant, mammalian cell cultures of the invention (adherent or non-adherent and growing or growth arrested), can be small scale cultures, such as for example in 100 ml containers having about 30 ml of media, 250 ml containers having about 80 to 90 ml of media, 250 ml containers having about 150 to 200 ml of media. Alternatively, the cultures can be large scale such as for example 1000 ml containers having about 300 to 1000 ml of media, 3000 ml containers having about 500 to 3000 ml of media, 8000 ml containers having about 2000 to about 8000 ml of media, and 15000 ml containers having about 4000 ml to about 15000 ml of media. Large scale cultures can also be bioreactors.

Optimal periods for which the cultures are in contact with vanadate are for longer than the typical period for one normal growth cycle (e.g., for Chinese hamster ovary cells (CHO cells), where one growth cycle has been reported to be approximately 20–22 hours (Rasmussen et al., (1998) Cytotechnology, 28:31–42)). As such, in a preferred embodiment, the cultures comprise vanadate preferably for at least about 20 hours, more preferably for about 22 hours, more preferably for about one day, more preferably for about 2 days, more preferably for about 3 days, more preferably for about 4 days, more preferably for about 5 days and even more preferably for about 7 days.

Additionally, the methods of the invention can be applied to perfused cell cultures. Perfused cell cultures are typically cultured continuously and can be grown for as little as about five days and for long as about nine months or longer, but are typically cultured for about 25 days. Thus, it is contemplated that vanadate can be included in perfused culture media either continuously, or intermittently over the course of the perfused culture run.

For the purposes of the invention, the cells may be growing or induced to stop growing, i.e., senescent, by a method or reagent commonly used in the art, e.g., radiation or drugs. Alternatively, the cells may become growth arrested by virtue of overgrowth and crowding in the container. Thus, the culture medium can comprise vanadate during either growth or senescence of the cells, including during passaging of cells, amplification of cells, growth of cells during recombinant polypeptide production stages, feeding of cell cultures during any of the foregoing, and/or during freezing and storage of cells. Further, in feeding of growing cultures, vanadate can be added in variable concentrations to pulse the culture with high concentrations, followed by a removal of the vanadate. For example, the cells can be grown during a proliferative phase in the absence of vanadate, and then in an induction phase in the presence of vanadate. Alternatively, vanadate can be present during both proliferative and induction phases.

Further, the methods of the invention can be used in combination with known or yet to be discovered methods of inducing the production of recombinant proteins. By "inducing conditions" is meant a technique to increase the relative production per cell of a desired recombinant protein. Such techniques include cold temperature shift, and additions of chemicals such as alkanoic acid (including butyrate compounds, as described in U.S. Pat. No. 5,705,364 to Etcheverry et al., incorporated herein by reference), DMSO, DMF, DMA, TNF-alpha, phorbol 12-myristate 13-acetate, PMA, propionate, forskolin, dibutyryl cAMP, 2-aminopurine, adenine, adenosine, okadaic acid, and combinations of any of these techniques, to name just a few examples, as well as any yet to be described and/or discovered induction techniques. Typically, a batch culture of cells at high density is induced to produce the recombinant protein. Often, other cell processes (such as growth and division) are inhibited so as to direct most of the cells' energy into recombinant protein production.

The invention finds particular use because it increases production of secreted recombinant polypeptides, in part because the cell cultures have increased numbers of viable cells. Additionally, the use of vanadate reduces the need to add growth factors to the medium, such as for example, insulin-like growth factor (IGF-1), thus, the cost of producing recombinant polypeptides are decreased. Further, by not adding a hormone polypeptide to the medium (i.e., a growth factor), isolating the secreted recombinant polypeptide of interest is simplified.

Tissue culture medium is defined, for purposes of the invention, as a medium suitable for growth of animal cells, and preferably mammalian cells, in in vitro cell culture. Typically, tissue culture medium contains a buffer, salts, energy source, amino acids, vitamins and trace essential elements. In addition, the medium can oftentimes require additional components such as growth factors, lipids, and/or other serum components (e.g., transferrin).

Any medium capable of supporting growth of animal cells in culture can be used; the invention is broadly applicable to animal cells in culture, particularly mammalian cells, and the choice of medium is not crucial to the invention. Tissue culture media suitable for use in the invention are commercially available from ATCC (Manassas, Va.). For example, any one or combination of the following media can be used: RPMI-1640 Medium, Dulbecco's Modified Eagle's Medium, Minimum Essential Medium Eagle, F-12K Medium, Iscove's Modified Dulbecco's Medium. Often, depending upon the requirements of the particular cell line used, medium also contains a serum additive such as Fetal Bovine Serum, or a serum replacement. Examples of serum-replacements (for serum-free growth of cells) are TCH™, TM-235™, and TCH™; these products are available commercially from Celox (St. Paul, Minn.). When defined medium that is serum-free and/or peptone-free is used, the medium is usually highly enriched for amino acids and trace elements (see, for example, U.S. Pat. No. 5,122,469 to Mather et al., and U.S. Pat. No. 5,633,162 to Keen et al.).

Serum adds to the expense of cell culture, and problems arise from variance between serum lots and serum quality, in addition, there are serious regulatory concerns about viral contamination in serum and further, removing serum proteins from downstream processing is burdensome, as such, in a preferred embodiment the medium is serum free or essentially free of serum and the recombinant polypeptide producing cell lines have been selected for growth without serum (Rasmussen et al., (1998) Cytotechnology 28:31–42). Essentially serum free media is meant to include very low amounts of serum in the culture media. This includes less than about 2% serum, more preferably less than about 1% serum, more preferably less than about 0.5% serum, and even more preferably less than about 0.25% serum. In another preferred embodiment, the recombinant cell line is a dihydrofolate reductase negative, CHO cell line, adapted for growth without serum.

Added to the medium is an effective amount of vanadate. An effective amount of vanadate is that amount that is capable of increasing cell survival of a culture and/or reducing the amount of growth hormone, such as for example, insulin-like growth factor (IGF-1), in the medium that is required for cell survival. Reduction of growth hormone can be measured by a reduction in the weight or volume of growth hormone normally delivered such that it is reduced by more than about 10%, more preferably more than about 20%, preferably about more than 30%, preferably more than about 40%, preferably more than about 50%, more preferably more than about 60%, more preferably more than about 70%, and even more preferably more than about 75%, or more.

Vanadate can be produced in different forms and is preferably a salt, in particular, sodium orthovanadate. Other preferred vanadates include but are not limited to peroxovanadate, diperoxovanadate, pervanadate and vanadium and all derivatives therefrom and therein.

A variety of vanadates are known in the art including orthovanadate, metavanadate, decavanadate, and can be in the form of monovalent metal salts with sodium, potassium, ammonium, or related salts. Further, vanadium salts can include vanadate complexes formed in the presence of hydrogen peroxide, to create what have been termed peroxovandaium complexes described in Posner et al., ((1994), J. of Biol. Chem., 269:4596–4604). The vanadium products can be either mono-peroxovanadates or di-peroxovanadates. The peroxovanadates were generated by mixing vanadate and hydrogen peroxide, followed by treatment with catalase to remove any peroxide that had not coordinated with the vanadium atom, which resulted in a number of different vanadium species, e.g., peroxovanadium-1,10-phenanthroline; peroxovanadium-4,7-dimethyl-1,10-phenanthroline, peroxovanadium-3,4,7,8,-tetramethyl-1,10-phenantronline, peroxovanadium-bipyridine, peroxovanadium-oxalic acid, peroxovanadium-pyridine-2-carboxlyic acid, peroxovanadium-5-hydrooxypyridine-2-carboxylic acid, peroxovanadium-2,6-pdc, and peroxovanadium-pyridine-2,6-dicarboxyclic acid. Many of these compounds were found to have up to 100 fold increased activity relative to orthovanadate. See also Huyer et al., (1997), J. of Biol. Chem., 272: 843–851.

The concentration of such compounds to use in the invention can be determined by those skilled in the art by, for example, comparing the cell death inhibitory activity of orthovanadate against that of a peroxovanadate, and extrapolating appropriate concentrations therefrom. The extrapolated concentrations can then be used as a starting point to determine the range of effective amounts of compound that should be added to a culture medium, which amounts can then be determined using small scale experiments such as those described herein. In preferred embodiments, the vanadate is orthovanadate and is in the culture medium at about 0.1 to 70 micromolar vanadate, more preferably about 1 to 50 micromolar vanadate, more preferably about 5 to 40 micromolar vanadate, and more preferably about 10 to 35 micromolar vanadate.

The invention finds particular utility in improving the production of recombinant polypeptides via cell culture processes. The cell lines used in the invention can be genetically engineered to express a polypeptide of commercial or scientific interest. By genetically engineered is meant that the cell line has been transfected, transformed or transduced with a recombinant polynucleotide molecule, and/or otherwise altered (e.g., by homologous recombination and gene activation) so as to cause the cell to express a desired recombinant polypeptide. Methods and vectors for genetically engineering cells and/or cell lines to express a polypeptide of interest are well known to those of skill in the art; for example, various techniques are illustrated in *Current Protocols in Molecular Biology*, Ausubel et al., eds. (Wiley & Sons, New York, 1988, and quarterly updates) and Sambrook et al., *Molecular Cloning: A Laboratory Manual* (Cold Spring Laboratory Press, 1989).

In some embodiments, the recombinant polypeptide of the invention is expressed from a vector comprising a nucleic acid sequence encoding the recombinant polypeptide, wherein the nucleic acid sequence is operably linked to a promoter and/or enhancer that is/are responsive to vanadate. In this context, when a promoter and/or enhancer are responsive to vanadate it is meant that vanadate increases the production of the recombinant polypeptide by increasing transcription relative to normal transcriptional activity of the nucleic acid operably linked to the same promoter/enhancer. Examples of vanadate responsive promoters include the HIV-1 LTR, which is strongly stimulated by peroxovanadium compounds (Barbeau et al., (1997) J. Biol. Chem., 272:12968–12977).

Particularly preferred polypeptides for expression are polypeptide-based drugs, also known as biologics. Preferably, the polypeptides are expressed as extracellular products, which can be either secreted into the culture medium or transmembrane, i.e., having a portion of the polypeptide extruding through the cell membrane into the extracellular milieu. Recombinant polypeptides that can be produced using the invention include but are not limited to Flt3 ligand, CD40 ligand, erythropoeitin, thrombopoeitin, calcitonin, Fas ligand, ligand for receptor activator of NF-kappa B (RANKL), TNF-related apoptosis-inducing ligand (TRAIL), ORK/Tek, thymic stroma-derived lymphopoietin, granulocyte colony stimulating factor, granulocyte-macrophage colony stimulating factor, mast cell growth factor, stem cell growth factor, epidermal growth factor, RANTES, growth hormone, insulin, insulinotropin, insulin-like growth factors, parathyroid hormone, nerve growth factors, glucagon, interleukins 1 through 18, colony stimulating factors, lymphotoxin-β, tumor necrosis factor, leukemia inhibitory factor, oncostatin-M, and various ligands for cell surface molecules Elk and Hek (such as the ligands for eph-related kinases, or LERKS). Descriptions of polypeptides that can be produced according to the invention may be found in, for example, *Human Cytokines: Handbook for Basic and Clinical Research, Vol. II* (Aggarwal and Gutterman, Eds. Blackwell Sciences, Cambridge Mass., 1998); *Growth Factors: A Practical Approach* (McKay and Leigh, Eds. Oxford University Press Inc., New York, 1993) and *The Cytokine Handbook* (AW Thompson, ed.; Academic Press, San Diego Calif.; 1991).

Production of the receptors for any of the aforementioned polypeptides can also be improved using the invention, including the receptors for both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or Apoptosis-Inducing Receptor (AIR). A particularly preferred receptor is a soluble form of the IL-1 receptor type II; such polypeptides are described in U.S. Pat. No. 5,767,064, incorporated herein by reference in its entirety.

Other polypeptides that can be produced using the invention include cluster of differentiation antigens (referred to as CD polypeptides), for example, those disclosed in *Leukocyte Typing VI (Proceedings of the VIth International Workshop and Conference*; Kishimoto, Kikutani et al., Eds. Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and OX40; the ligands are often members of the TNF family (as are 41BB ligand and OX40 ligand); accordingly, members of the TNF and TNFR families can also be produced using the present invention.

Polypeptides that are enzymatically active can also be produced according to the instant invention. Examples include metalloproteinase-disintegrin family members, various kinases, glucocerebrosidase, alpha-galactosidase A, superoxide dismutase, tissue plasminogen activator, Factor VIII, Factor IX, apolipoprotein E, apolipoprotein A-I, globins, an IL-2 antagonist, alpha-1 antitrypsin, TNF-alpha Converting Enzyme, and numerous other enzymes. Ligands for enzymatically active polypeptides can also be produced by applying the instant invention.

The inventive compositions and methods are also useful for production of other types of recombinant polypeptides, including immunoglobulin molecules or portions thereof, and chimeric antibodies (i.e., an antibody having a human constant region couples to a murine antigen binding region) or fragments thereof. Numerous techniques are known by which DNA encoding immunoglobulin molecules can be manipulated to yield DNAs capable of encoding recombinant polypeptides such as single chain antibodies, antibodies with enhanced affinity, or other antibody-based polypeptides (see, for example, Larrick et al., 1989, Biotechnology 7:934–938; Reichmann et al., 1988, Nature 332:323–327; Roberts et al., 1987, Nature 328:731–734; Verhoeyen et al., 1988, Science 239:1534–1536; Chaudhary et al., 1989, Nature 339:394–397). Recombinant cells producing fully human antibodies (such as are prepared using transgenic animals, and optionally further modified in vitro), as well as humanized antibodies can also be used in the invention. The term humanized antibody also encompasses single chain antibodies. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. For example, the invention can be used to induce the expression of human and/or humanized antibodies that immunospecifically recognize specific cellular targets, e.g., any of the aforementioned polypeptides, the human EGF receptor, the her-2/neu antigen, the CEA antigen, Prostate Specific Membrane Antigen (PSMA), CD5, CD11a, CD18, NGF, CD20, CD45, Ep-cam, other cancer cell surface molecules, TNF-alpha, TGF-b1, VEGF, other cytokines, alpha 4 beta 7 integrin, IgEs, viral polypeptides (for example, cytomegalovirus), etc., to name just a few.

Various fusion polypeptides can also be produced using the invention. A fusion polypeptide is a polypeptide, or domain or a polypeptide (e.g. a soluble extracellular domain) fused to a heterologous polypeptide or peptide. Examples of such fusion polypeptides include polypeptides expressed as a fusion with a portion of an immunoglobulin molecule, polypeptides expressed as fusion polypeptides with a zipper moiety, and novel polyfunctional polypeptides such as a fusion polypeptides of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion polypeptide and a zipper fusion polypeptide, respectively; the techniques discussed therein are applicable to other polypeptides. Another fusion polypeptide is a recombinant TNFR:Fc, also known as "entanercept." Entanercept is a dimer of two molecules of the extracellular portion of the p75 TNF alpha receptor, each molecule consisting of a 235 amino acid TNFR-derived polypeptide that is fused to a 232 amino acid Fc portion of human IgG1. In fact, any of the previously described molecules can be expressed as a fusion polypeptide including but not limited to the extracellular domain of a cellular receptor molecule, an enzyme, a hormone, a cytokine, a portion of an immunoglobulin molecule, a zipper domain, and an epitope.

The resulting expressed polypeptide can then be collected. In addition the polypeptide can purified, or partially purified, from such culture or component (e.g., from culture medium or cell extracts or bodily fluid) using known processes. By "partially purified" means that some fractionation procedure, or procedures, have been carried out, but that more polypeptide species (at least 10%) than the desired polypeptide is present. By "purified" is meant that the polypeptide is essentially homogeneous, i.e., less than 1% contaminating polypeptides are present. Fractionation procedures can include but are not limited to one or more steps of filtration, centrifugation, precipitation, phase separation, affinity purification, gel filtration, ion exchange chromatography, hydrophobic interaction chromatography (HIC; using such resins as phenyl ether, butyl ether, or propyl ether), HPLC, or some combination of above.

The invention also optionally encompasses further formulating the polypeptides. By the term "formulating" is meant that the polypeptides can be buffer exchanged, sterilized, bulk-packaged and/or packaged for a final user. For purposes of the invention, the term "sterile bulk form" means that a formulation is free, or essentially free, of microbial contamination (to such an extent as is acceptable for food and/or drug purposes), and is of defined composition and concentration. The term "sterile unit dose form" means a form that is appropriate for the customer and/or patient administration or consumption. Such compositions can comprise an effective amount of the polypeptide, in combination with other components such as a physiologically acceptable diluent, carrier, or excipient. The term "physiologically acceptable" means a non-toxic material that does not interfere with the effectiveness of the biological activity of the active ingredient(s).

The invention having been described, the following examples are offered by way of illustration and not limitation.

EXAMPLE

Dose Response Effect of Orthovanadate in Culture Medium

In this experiment, the effect of adding various concentrations of vanadate was tested in mammalian cell shake flask cultures. A Chinese Hamster Ovary (CHO) cell line that had been genetically engineered to produce huTNFR:Fc (a soluble form of the human tumor necrosis factor alpha receptor extracellular domain fused to an Fc polypeptide from an immunogolublin see in U.S. Pat. No. 5,945,397) was grown in serum-free medium. A dose response analysis was performed to determine an optimal dose for vanadate. Table 1 shows the effect of sodium orthovanadate on viability and viable cell density when titrated from 0 to 50 $\mu$M. Concentrations between about 10 $\mu$M and 35 $\mu$M appear most effective (viable cell density×106 is VCD x$10^6$).

TABLE 1

Dose Response of Vanadate

| Conc. Vanadate | Day | VCD, x$10^6$ | % Viability |
|---|---|---|---|
| 0 | 0 | 2 | 98 |
|   | 5 | 4.493 | 69 |
| 0 | 0 | 2 | 98 |
|   | 5 | 4.017 | 68 |
| 10 uM | 0 | 2 | 98 |
|   | 5 | 5.102 | 80 |
| 10 uM | 0 | 2 | 98 |
|   | 5 | 6.796 | 89 |
| 20 uM | 0 | 2 | 98 |
|   | 5 | 5.8 | 90 |
| 35 uM | 0 | 2 | 98 |
|   | 5 | 5.142 | 87 |
| 35 uM | 0 | 2 | 98 |
|   | 5 | 5.184 | 90 |
| 50 uM | 0 | 2 | 98 |
|   | 5 | 4.136 | 83 |
| 50 uM | 0 | 2 | 98 |
|   | 5 | 3.625 | 81 |

A second experiment was performed to test the effects of sodium orthovanadate on specific production of the recombinant polypeptide huTNFR-Fc, expressed from cells when compared to the same cells grown without vanadate. Flasks were inoculated at 2×$10^6$ cells/ml and were either grown without additional compounds or with sodium butyrate at 0.5 mM or sodium butyrate with sodium orthovanadate at 20 $\mu$M. Flasks were set up in an incubator at 31° C. Measurements for cell concentration and viability were taken using a hemacytometer and the trypan blue dye exclusion method and the results are shown in Table 2. Production of huTNFR-Fc was measured by standard ELISA.

TABLE 2

Effect of Sodium Orthovanadate on Cultures Expressing huTNFR-Fc.

| Inducing Agent | Conc. | Day | VCD, x$10^6$ | % Viability | Titer | Specific Productivity |
|---|---|---|---|---|---|---|
| None |   | 0 | 2 | 96 | 100% | 100% |
|   |   | 5 | 6.651 | 79 |   |   |
| NaButyrate | 0.5 mM | 0 | 2 | 96 | 125% | 153% |
|   |   | 5 | 5.067 | 78 |   |   |
| NaButyrate | 0.5 mM | 0 | 2 | 96 | 140% | 161% |
|   |   | 5 | 5.547 | 78 |   |   |
| Butyrate + Vanadate | 0.02 mM | 0 | 2 | 96 | 158% | 165% |
|   |   | 5 | 6.313 | 94 |   |   |
| Butyrate + Vanadate | 0.02 mM | 0 | 2 | 96 | 140% | 148% |
|   |   | 5 | 6.26 | 95 |   |   |

The data in Table 2 shows that the presence of vanadate resulted in a higher percentage of viable cells when compared to untreated recombinant cells. In addition, the total production of the recombinant polypeptide was improved substantially over untreated cell cultures and was still higher than cells treated with butyrate alone. In table 2, the 'titer' and 'specific productivity' data for cells grown without vanadate was normalized to 100% as a baseline, subsequently, the increase over baseline of recombinant production of TNFR-Fc in the presence of butyrate or butyrate plus vanadate is shown. The increase in cell viability is significant whether butyrate is added or not, and the most dramatic results were observed with 20 $\mu$M vanadate in the culture, where the viable cell concentration improved from 79% in untreated cells to 95% in vanadate treated cells and in addition, vanadate also increased the total number of cells on day 5.

EXAMPLE

Reduced Growth Factor Concentration in the Presence of Vanadate

Vanadate can also reduce the requirement for growth factors to maintain recombinant cell viability. Table 3 shows the effect of reducing the concentration of insulin like growth factor (IGF-1) on viability in the presence and absence of vanadate. At 5 ng/L with vanadate, IGF-1 is sufficient to maintain the same viability of recombinant polypeptide producing cells as 100 $\mu$g/L IGF-1 in the absence of vanadate. FIG. 1 shows the effect of vanadate on a bioreactor culture with reduced IGF-1 (25 $\mu$g/L) compared with normal IGF-1 (100 $\mu$g/L). These data demonstrate a significantly enhanced viability in the presence of vanadate with these cultures.

TABLE 3

Effect of Vanadate and Reduced IGF-1 on Recombinant CHO Cells.

| IGF-1 | Sodium orthovanadate | cells/ml | % viable |
|---|---|---|---|
| 5 ng/L | − | 3.936 | 58 |
| 5 ng/L | + | 4.916 | 73 |
| 100 µg/L | − | 5.825 | 74 |
| 100 µg/L | + | 6.806 | 90 |

Furthermore, when 100 mg/L of IGF-1 was added to media and compared to the effect of 25 mg/L of IGF-1 with 20 µM sodium orthovanadate media, cell viability was improved in the vanadate containing media after four days and after six days there was markedly more cell survival in the presence of vanadate.

The results from these experiments show how adding vanadate, in this case orthovanadate, can be applied in mammalian cell culture for a number of purposes. Cell viability is increased in cultures having 20 µM orthovanadate compared to cells grown without orthovanadate over a five day period (FIG. 1). In short, adding vanadate, such as orthovanadate, helps to create a more efficient mammalian cell culture process by reducing cell death, reducing the requirement of growth factors in the cell culture and increasing secreted polypeptide production.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method comprising culturing a cell line recombinantly engineered to express a polypeptide of interest, wherein the cell line is cultured in medium comprising an effective amount of vanadate, whereby cell survival is increased and recovery of the secreted polypeptide of interest is increased relative to cells grown without vanadate.

2. The method of claim 1, wherein the recombinantly engineered cell line is a mammalian cell line.

3. The method of claim 2, wherein the mammalian cells are selected from the group consisting of CHO, VERO, BHK, HeLa, COS, MDCK, 293, 3T3, a myeloma cell line, a hybridoma cell line, and W138 cells.

4. The method of claim 3, wherein the recombinantly engineered cell line is grown for at least 20 hours.

5. The method of claim 3, wherein the medium is serum free.

6. The method of claim 3, wherein the medium contains less than about 100 µg/L of IGF-1.

7. The method of claim 6, wherein the medium contains about 25 µg/L of insulin-like growth factor (IGF-1).

8. The method of claim 3, wherein the recombinantly engineered cell line is grown in a proliferative phase in the absence of vanadate and subsequently in an induction phase for recombinant polypeptide production in the presence of vanadate.

9. The method of claim 8, wherein the vanadate is a peroxovanadate.

10. The method of claim 9, wherein the peroxovanadate is selected from the group consisting of monoperoxovanadate (VL) and diperoxovanadate (VL$_2$).

11. The method of claim 8, wherein the vanadate is sodium orthovanadate.

12. The method of claim 11, wherein the sodium orthovanadate is at a concentration of between about 1 µM to about 50 µM.

13. The method of claim 12, wherein the sodium orthovanadate is at a concentration of above about 10 µM.

14. The method of claim 12, wherein the sodium orthovanadate is at a concentration of above about 20 µM.

15. The method of claim 12, wherein the sodium orthovanadate is at a concentration of about 35 µM.

16. The method of claim 15, wherein the recombinantly engineered cells produce a polypeptide of interest which is selected from the group consisting of a soluble TNF receptor, a soluble IL-4 receptor, a soluble IL-1 type 11 receptor, a soluble flt3 ligand, a soluble CD40 ligand, an erythropoeitin, an antibody, an Fc-fusion polypeptide, a calcitonin, a growth hormone, an insulinotropin, a parathyroid hormone, an interferons, a nerve growth factor, a glucagon, an interleukins, a colony stimulating factor, a glucocerebrosidase, a superoxide dismutase, a tissue plasminogen activator, a Factor VIII, a Factor IX, an apolipoprotein E, an apolipoprotein A-I, a globin, an IL-2 receptor, an IL-2 antagonist, alpha-1 antitrypsin, and an alpha-galactosidase A.

17. The method of claim 16, wherein the cell line is cultured in a bioreactor.

18. The method of claim 17, wherein the cell line is cultured in suspension cultures.

19. The method of claim 17, further comprising collecting the polypeptide of interest.

20. A cell culture comprising a cell line recombinantly engineered to secrete a polypeptide of interest, a culture medium and an effective amount of vanadate sufficient to increase cell viability and to increase recovery of the polypeptide of interest.

21. The cell culture of claim 20, wherein the recombinantly engineered cell line is a mammalian cell line.

22. The cell culture of claim 21, wherein the mammalian cell line is selected from the group consisting of CHO, VERO, BHK, HeLa, COS, MDCK, 293, 3T3, a myeloma cell line, a hybridoma cell line, and W138 cells.

23. The cell culture of claim 22, wherein the recombinantly engineered cell line is grown for at least 20 hours.

24. The cell culture of claim 22, wherein the culture medium is serum free.

25. The cell culture of claim 22, wherein the culture medium contains about 25 µg/L of insulin-like growth factor (IGF-1).

26. The cell culture of claim 22, wherein the culture medium contains from about 25 µg/L to less than about 100 µg/L IGF-1.

27. The cell culture of claim 22, wherein the recombinantly engineered cell line is grown in a proliferative phase in the absence of vanadate and subsequently in an induction phase for recombinant polypeptide production in the presence of vanadate.

28. The cell culture of claim 27, wherein the vanadate is a peroxovanadate.

29. The cell culture of claim 28, wherein the peroxovanadate is selected from the group consisting of monoperoxovanadate (VL) and diperoxovanadate (VL2).

30. The cell culture of claim 27 wherein the vanadate is sodium orthovanadate.

31. The cell culture of claim 30, wherein the sodium orthovanadate is at a concentration of between about 1 $\mu$M to about 50 $\mu$M.

32. The cell culture of claim 31, wherein the sodium orthovanadate is at a concentration of above about 10 $\mu$M.

33. The cell culture of claim 32, wherein the sodium orthovanadate is at a concentration of above about 20 $\mu$M.

34. The cell culture of claim 33, wherein the sodium orthovanadate is at a concentration of about 35 $\mu$M.

35. The cell culture of claim 34, wherein the recombinantly engineered cells produce a polypeptide of interest which is selected from the group consisting of a soluble TNF receptor, a soluble IL-4 receptor, a soluble IL-1 type II receptor, a soluble flt3 ligand, a soluble CD40 ligand, an erythropoeitin, an antibody, an Fc-fusion polypeptide, a calcitonin, a growth hormone, an insulinotropin, a parathyroid hormone, an interferons, a nerve growth factor, a glucagon, an interleukins, a colony stimulating factor, a glucocerebrosidase, a superoxide dismutase, a tissue plasminogen activator, a Factor VIII, a Factor IX, an apolipoprotein E, an apolipoprotein A-I, a globin, an IL-2 receptor, an IL-2 antagonist, alpha-1 antitrypsin, and an alpha-galactosidase A.

36. The cell culture of claim 35, wherein the cell line is cultured in bioreactors.

37. The cell culture of claim 36, further comprising collecting the polypeptide of interest.

38. The cell culture of claim 36, wherein the cell line is grown in suspension.

* * * * *

UNITED STATES PATENT AND TRADEMARK OFFICE
CERTIFICATE OF CORRECTION

PATENT NO. : 6,974,681 B1 Page 1 of 1
APPLICATION NO. : 10/226669
DATED : December 13, 2005
INVENTOR(S) : Jeffrey T. McGrew It is certified that error appears in the above-identified patent and that said Letters Patent is hereby corrected as shown below:

On Title Page Item (75):

"Jeffrey T McGrew" should be -- Jeffrey T. McGrew --.

Signed and Sealed this

First Day of May, 2007

JON W. DUDAS
*Director of the United States Patent and Trademark Office*